United States Patent [19]

Meier et al.

[11] Patent Number: 4,919,832
[45] Date of Patent: Apr. 24, 1990

[54] N-SUBSTITUTED TETRAHYDROQUINOLINES FOR USE AS ANTIOXIDANTS IN LUBRICANTS

[75] Inventors: Hans R. Meier; Samuel Evans, both of Marly, Switzerland

[73] Assignee: Ciba-Geigy Corporation, Ardsley, N.Y.

[21] Appl. No.: 305,037

[22] Filed: Feb. 2, 1989

Related U.S. Application Data

[62] Division of Ser. No. 135,964, Dec. 21, 1987, Pat. No. 4,828,741.

[51] Int. Cl.$^5$ ............................................. C10M 133/40
[52] U.S. Cl. .......................................... 252/50; 252/51; 252/51.5 R; 252/77; 252/405
[58] Field of Search ...................... 252/50, 51, 51.5 R, 252/77, 405

[56] References Cited

U.S. PATENT DOCUMENTS

| | | | |
|---|---|---|---|
| 2,647,824 | 8/1953 | Jones et al. | 44/63 |
| 2,846,435 | 8/1958 | Harris | 260/289 |
| 3,247,211 | 4/1966 | Weaver et al. | 260/287 |
| 3,833,400 | 9/1974 | Matsukawa et al. | 117/36.2 |
| 4,692,258 | 9/1987 | Rasberger et al. | 252/50 |
| 4,828,741 | 5/1989 | Meier et al. | 252/51.5 R |

OTHER PUBLICATIONS

Chem. Abstract 211626 (1958).

Primary Examiner—William R. Dixon, Jr.
Assistant Examiner—Jerry D. Johnson
Attorney, Agent, or Firm—Luther A. R. Hall

[57] ABSTRACT

Composition containing
(a) at least one lubricant, hydraulic oil or metal-working fluid based on mineral oil or synthetic oils and
(b) 0.05–5% by weight, based on the total weight of the lubricant, hydraulic oil or metal-working fluid composition, of at least one compound of the formula V

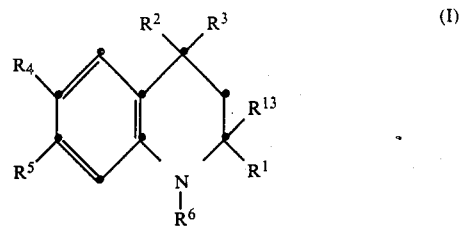

(I)

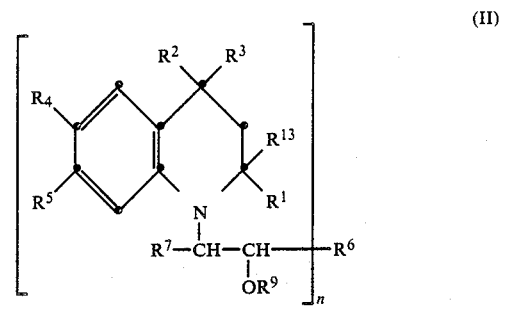

(II)

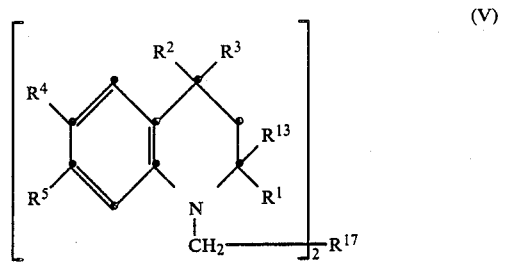

(V)

where $R^1$ and $R^2$ are independently alkyl, aryl, substituted aryl or benzyl, $R^3$ is hydrogen or methyl, $R^4$ and $R^5$ are independently hydrogen, methyl, methoxy, chloro or nitro, $R^{13}$ is hydrogen or methyl, and $R^{17}$ is a direct bond, alkylene or vinylene.

3 Claims, No Drawings

N-SUBSTITUTED TETRAHYDROQUINOLINES FOR USE AS ANTIOXIDANTS IN LUBRICANTS

This is a divisional of application Ser. No. 135,964, filed on Dec. 21, 1987, now U.S. Pat. No. 4,828,741, issued on May 9, 1989.

The present invention relates to lubricant, hydraulic oil or metal-working fluid compositions containing as stabilizers N-substituted 1,2,3,4-tetrahydroquinolines, to novel N-substituted 1,2,3,4-tetrahydroquinolines, and to the use of such N-substituted 1,2,3,4-tetrahydroquinolines as stabilizers in lubricants, hydraulic oils and metal-working fluids.

In general, various additives are added to mineral and synthetic lubricants, hydraulic oils or metal-working fluids to improve their performance characteristics. In particular there is a demand for additives which actively inhibit the oxidation or ageing of the lubricant, hydraulic oil or metal-working fluid and thus extend their life.

EP-A-72,349 discloses N-unsubstituted 1,2,3,4-tetrahydroquinolines for use as antioxidants in lubricants. DE-A-2,156,371 describes N-substituted 1,2,3,4-tetrahydroquinoline derivatives for use as stabilizers in colour former compositions for pressure-sensitive recordings. Furthermore, 1-amino- or 1-hydroxyalkyl-1,2,3,4-tetrahydroquinolines are described in U.S.-A-3,247,211 as starting materials for dyes. Moreover, U.S.-A-2,846,435 discloses N-alkyl-1,2,3,4-tetrahydroquinolines for use as rubber stabilizers, and GB-A-795,497 discloses N-substituted 1,2,3,4-tetrahydroquinolines for use as flexibility improvers for polymeric polyolefin coatings on metals.

The present invention accordingly provides a composition containing
  (a) at least one lubricant, hydraulic oil or metal-working fluid based on mineral oil or synthetic oils and
  (b) 0.05–5% by weight, based on the total weight of the lubricant, hydraulic oil or metal-working fluid composition, of at least one compound of the formulae I, II or/and V

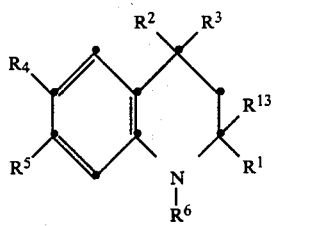
(I)

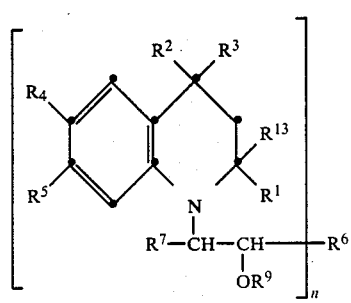
(II)

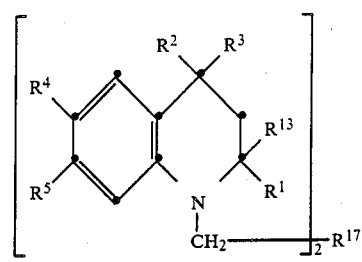
(V)

in which $R^1$ and $R^2$ are independently of each other $C_1$–$C_8$-alkyl, unsubstituted or $C_1$–$C_{12}$-alkyl-, Cl-, Br-, I-, $NO_2$-, OH- or $C_1$–$C_{12}$-alkoxy-substituted phenyl or naphthyl, or benzyl, $R^3$ is hydrogen or methyl, $R^4$ and $R^5$ are independently of each other hydrogen, methyl, methoxy, —Cl or —$NO_2$ and $R^4$ additionally in the formula I is a radical of the formula III

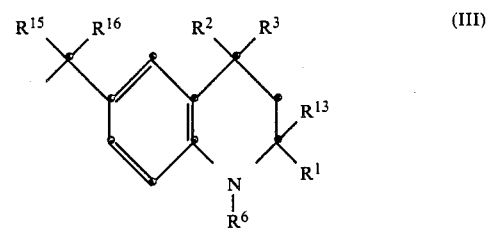
(III)

in which $R^{15}$ and $R^{16}$ are independently of each other hydrogen, $C_1$–$C_9$-alkyl, unsubstituted or $C_1$–$C_{12}$-alkyl-substituted phenyl, or benzyl, α-methylbenzyl or α,α-dimethylbenzyl, or $R^{15}$ and $R^{16}$ are together with the C atom to which they are bonded a 5-, 6- or 7-ring, with the proviso that when $R^4$ is a radical of the formula III $R^5$ is hydrogen, and in which furthermore $R^6$ is $C_1$–$C_{18}$-alkyl, $C_3$–$C_{18}$-alkenyl, $C_7$–$C_{12}$ aralkyl, $C_7$–$C_{12}$-alkaryl or $C_1$–$C_{12}$-alkyl-, Cl-, Br-, I-, $NO_2$-, OH- or $C_1$–$C_{12}$-alkoxy-ringsubstituted benzyl, $R^7$ is hydrogen or methyl, $R^8$, if n is 1, is hydrogen, $CH_2OR^{14}$, $C_1$–$C_{18}$-alkyl, phenyl or —$CH_2SR^{14}$ or, if n is 2 to 4, a radical of the formulae

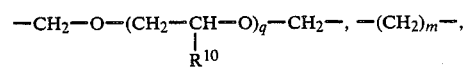

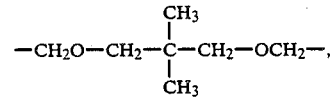

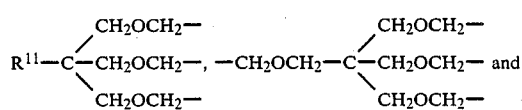

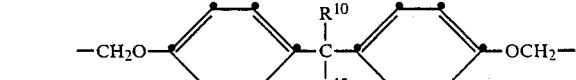

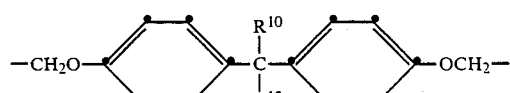

and in which furthermore $R^9$ is hydrogen, methyl,

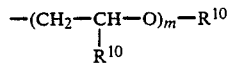

or

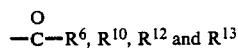

are independently of one another hydrogen or methyl, $R^{11}$ is hydrogen, methyl or ethyl and $R^{14}$ is $C_1$-$C_{18}$-alkyl, $C_7$-$C_{13}$-alkaryl, phenyl, naphthyl, pentalyl, heptalyl, indacyl or unsubstituted or $C_1$-$C_{12}$-alkyl-, Cl-, Br-, I-, $NO_2$-, OH- or $C_1$-$C_{12}$-alkoxy-ringsubstituted benzyl, n is a number from 1 to 4, m and q are numbers from 1 to 10, p is a number from 2 to 10, and $R^{17}$ is either $C_xH_{2x}$, where x is 0 to 10, or —CH=CH—.

A $C_1$-$C_8$-alkyl $R^1$ or $R^2$ is a straight-chain or branched alkyl radical, for example methyl, ethyl, n-propyl, isopropyl, n-butyl, isobutyl, sec.-butyl, tert.-butyl, straight-chain or branched pentyl, hexyl, heptyl or octyl.

A $C_1$-$C_9$-alkyl $R^{15}$ or $R^{16}$ is a straight-chain or branched alkyl radical, for example methyl, ethyl, n-propyl, isopropyl, n-butyl, isobutyl, sec.-butyl, tert.-butyl, straight-chain or branched pentyl, hexyl, heptyl, octyl or nonyl.

A $C_1$-$C_{18}$-alkyl $R^6$, $R^8$ or $R^{14}$ is a straight-chain or branched alkyl radical, for example methyl, ethyl, n-propyl, isopropyl, n-butyl, isobutyl, sec.-butyl, tert.-butyl, straight-chain or branched pentyl, hexyl, heptyl, octyl, nonyl, decyl, undecyl, dodecyl, tridecyl, tetradecyl, pentadecyl, hexadecyl, heptadecyl or octadecyl. $R^8$ is preferably $C_1$-$C_{12}$-alkyl.

A $C_3$-$C_{18}$-alkenyl $R^6$ is a straight-chain or branched alkenyl radical which contains one or more, but preferably one double bond, for example allyl, n-butenyl, 1,3-butadienyl, i-pentenyl, pentenyl, hexenyl, heptenyl, octenyl, nonenyl, decenyl, undecenyl, dodecenyl, tridecenyl, 2-nonyl-2-butenyl, tetradecenyl, pentadecenyl, hexadecenyl, 8-heptadecenyl, 2-octadecenyl or oleyl. Preference is given to allyl or oleyl, in particular allyl.

In a $C_1$-$C_{12}$-alkyl-substituted phenyl $R^1$, $R^2$, $R^{15}$ or $R^{16}$ and a $C_1$-$C_{12}$-alkyl-ringsubstituted benzyl $R^6$ or $R^{14}$, the phenyl or benzyl radical can be monosubstituted or polysubstituted, preferably monosubstituted or disubstituted, in the case of $R^{15}$ and $R^{16}$, however, only monosubstituted. $C_1$-$C_{12}$-Alkyl is for example methyl, ethyl, n-propyl, isopropyl, n-butyl, isobutyl, sec.-butyl, tert.-butyl, straightchain or branched nonyl or dodecyl.

In a $C_1$-$C_{12}$-alkoxy-substituted phenyl $R^1$ or $R^2$ and a $C_1$-$C_{12}$-alkoxy-ringsubstituted benzyl $R^6$ or $R^{14}$, the phenyl or benzyl radical can be monosubstituted or polysubstituted, but preferably monosubstituted or disubstituted; $C_1$-$C_{12}$-alkoxy is, for example, methoxy, ethoxy, n-propoxy, isopropoxy, n-butoxy, isobutoxy, sec.-butoxy, tert.-butoxy, straightchain or branched nonyloxy or dodecyloxy.

A $C_7$-$C_{12}$-aralkyl $R^6$, preferably phenyl-$C_1$-$C_4$-alkyl, is, for example, benzyl, 1- or 2-phenethyl, 3-phenyl-propyl, α,α-dimethylbenzyl, 2-phenylisopropyl, 2-phenylhexyl or naphthylmethyl. Preference is given to benzyl and α,α-dimethylbenzyl, in particular benzyl.

In a $C_7$-$C_{12}$-alkaryl $R^6$ and a $C_7$-$C_{13}$-alkaryl $R^{14}$, the aryl radical is phenyl or naphthyl, but preferably phenyl, which are each monosubstituted or polysubstituted, preferably monosubstituted or disubstituted, by $C_1$-$C_6$-alkyl and $C_1$-$C_7$-alkyl respectively, preferably by $C_1$-$C_4$-alkyl, e.g. 2,4,6-trimethylphenyl, 2,4-dimethylphenyl, 4-isopropylphenyl, 4-hexylphenyl, 4-methylphenyl, 3,4-diethylphenyl, 2-methylnaphthyl or 2,6-dimethylnaphthyl. However, preference is given to 2,5-dimethylphenyl and 4-methylphenyl, in particular 4-methylphenyl.

Preference is given to a composition containing as component (b) at least one compound of the formulae I or/and II in which $R^1$ and $R^2$ are independently of each other $C_1$-$C_8$-alkyl or benzyl, particularly preferably $C_1$-$C_8$-alkyl, very especially preferably $C_1$-$C_4$-alkyl, in particular methyl or ethyl.

Preference is likewise given to a composition containing as component (b) at least one compound of the formulae I or/and II in which $R^3$ is hydrogen.

Also of interest is a composition containing as component (b) at least one compound of the formulae I or/and II in which $R^4$ and $R^5$ are independently of each other hydrogen or methyl.

Of particular interest is a composition containing as component (b) at least one compound of the formula I in which $R^4$ is a radical of the formula III

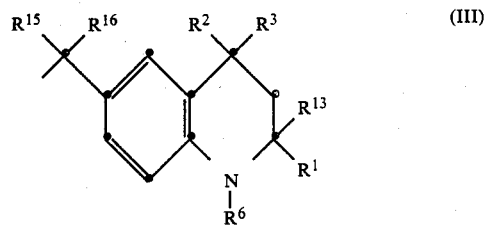

Of similar interest is a composition containing as component (b) at least one compound of the formula I in which $R^6$ is $C_1$-$C_{12}$-alkyl, $C_3$-$C_8$-alkenyl or benzyl, but preferably $C_1$-$C_4$-alkyl, allyl, methallyl or benzyl.

Also of interest is a composition containing as component (b) at least one compound of the formula II in which $R^7$ is hydrogen.

A further embodiment is a composition containing as component (b) at least one compound of the formula II in which $R^8$ is hydrogen, $C_1$-$C_4$-alkyl, phenyl, —CH$_2$O—(CH$_2$)$_p$—OCH$_2$, —CH$_2$O—(CH$_2$—CH$_2$—O)$_q$—CH$_2$—, —(CH$_2$)$_m$—,

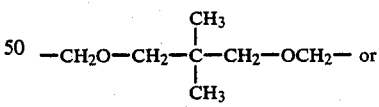

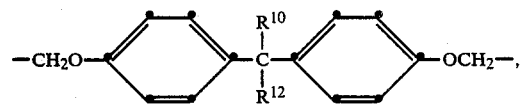

but preferably hydrogen or methyl, and n is 1 or 2.

A specific embodiment is a composition containing as component (b) at least one compound of the formula II in which $R^9$ is hydrogen, methyl,

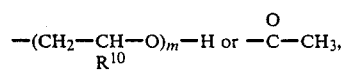

but preferably hydrogen.

A similarly interesting embodiment is a composition containing as component (b) at least one compound of the formulae I or/and II in which $R^{13}$ is methyl.

A particular embodiment is a composition containing as component (b) at least one compound of the formula II in which n is 1 or 2.

An additional embodiment is a composition containing as component (b) at least one compound of the formula II in which m, p and q are independently of one another a number from 2 to 6.

The present invention further provides the novel compounds N-(2-hydroxypropyl)-2,2,4,7-tetramethyl-1,2,3,4-tetrahydroquinoline, N-[2-hydroxy-3-(tert.-nonylthio)-propyl]-2,2,4-trimethyl-1,2,3,4-tetrahydroquinoline, N-[2-hydroxy-3-(tert.-nonylthio)-propyl]-2,2,4,6-tetramethyl-1,2,3,4-tetrahydroquinoline.

The present invention likewise provides the novel compounds of the formula IV

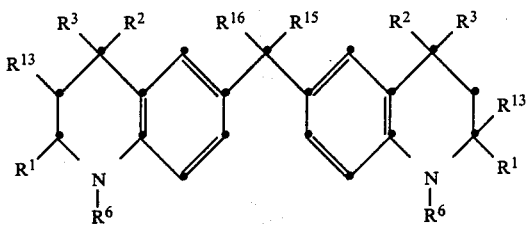

in which $R^1$ and $R^2$ are independently of each other $C_1$–$C_8$-alkyl, unsubstituted or $C_1$–$C_{12}$-alkyl, Cl-, Br-, I-, $NO_2$-, OH- or $C_1$–$C_{12}$-alkoxy-substituted phenyl or naphthyl, or benzyl, $R^3$ is hydrogen or methyl, $R^6$ is $C_1$–$C_{18}$-alkyl, $C_3$–$C_8$-alkenyl, $C_7$–$C_{12}$-aralkyl, $C_7$–$C_{12}$-alkaryl or $C_1$–$C_{12}$-alkyl-, Cl-, Br-, I-, $NO_2$-, OH- or $C_1$–$C_{12}$-alkoxy-ring-substituted benzyl, $R^{13}$ is hydrogen or methyl, $R^{15}$ and $R^{16}$ are independently of each other hydrogen, $C_1$–$C_9$-alkyl, unsubstituted or $C_1$–$C_{12}$-alkyl-substituted phenyl, benzyl, α-methylbenzyl or α,α-dimethylbenzyl, or in which $R^{15}$ and $R^{16}$ together with the C atom to which they are bonded are a 5-, 6- or 7-ring.

Specific preference is given to the compounds of the formula IV in which $R^{15}$ and $R^{16}$ together with the C atom to which they are bonded are a 5-, 6- or 7-ring, or $R^{15}$ and $R^{16}$ are independently of each other hydrogen or $C_1$–$C_4$-alkyl.

Examples of compounds of the formulae I and II are: 1,2,2,4-tetramethyl-1,2,3,4-tetrahydroquinoline, 1-ethyl-2,2,4-trimethyl-1,2,3,4-tetrahydroquinoline, 1,2-dimethyl-2,4-diethyl-1,2,3,4-tetrahydroquinoline, 2-methyl-1,2,4-triethyl-1,2,3,4-tetrahydroquinoline, 1-benzyl-2,2,4-trimethyl-1,2,3,4-tetrahydroquinoline, 1-allyl-2,2,4-trimethyl-1,2,3,4-tetrahydroquinoline, 1-benzyl-2,2,4,6,7-pentamethyl-1,2,3,4-tetrahydroquinoline, 1-butyl-2,2,4-trimethyl-1,2,3,4-tetrahydroquinoline, 1-(2-hydroxyethyl)-2,2,4-trimethyl-1,2,3,4-tetrahydroquinoline, 1-(2-hydroxypropyl)-2,2,4-trimethyl-1,2,3,4-tetrahydroquinoline, 1-(2-acetoxypropyl)-2,2,4,6-tetramethyl-1,2,3,4-tetrahydroquinoline, 1-(2-hydroxyethyl)-2,2,4,6-tetramethyl-1,2,3,4-tetrahydroquinoline, 1-(2-hydroxyethyl)-2,4-diethyl-2-methyl-1,2,3,4-tetrahydroquinoline, 1-(2-hydroxyethyl)-2,2,4,7-tetramethyl-1,2,3,4-tetrahydroquinoline, 1-(2-hydroxypropyl)-2,4-diethyl-2-methyl-1,2,3,4-tetrahydroquinoline, 1-(2-acetoxyethyl)-2,2,4-trimethyl-1,2,3,4-tetrahydroquinoline, 1-(β-methallyl)-2,2,4-trimethyl-1,2,3,4-tetrahydroquinoline, 1,16-bis-[2,2,4-trimethyl-1,2,3,4-tetrahydroquinol-1-yl]-2,15-dihydroxy-4,13-dioxa-hexadecane, 1,16-bis-[2,2,4-trimethyl-1,2,3,4-tetrahydroquinol-1-yl]-2,15-dihydroxy-4,7,10,13-tetraoxa-hexadecane, 1,14-bis-[2,2,4-trimethyl-1,2,3,4-tetrahydroquinol-1-yl]-2,13-dihydroxy-4,11-dioxatetradecane, 1,13-bis-[2,2,4-trimethyl-1,2,3,4-tetrahydroquinol-1-yl]-2,12-dihydroxy-4,7,10-trioxa-tridecane, 1,10-bis-[2,4-diethyl-2-methyl-1,2,3,4-tetrahydroquinol-1-yl]-2,9-dihydroxy-4,7-dioxa-decane, 2,2-di-{4-[3′-(2,2,4-trimethyl-1,2,3,4-tetrahydroquinol-1-yl)-2′-hydroxy-prop-1′-oxy]-phenyl}-propane, 1,1-di-{4-[3′-(2,2,4,6-tetramethyl-1,2,3,4-tetrahydroquinol-1-yl)-2′-hydroxy-prop-1′-oxy]-phenyl}-methane, 1-[2,2,4-trimethyl-1,2,3,4-tetrahydroquinol-1-yl]-3-(tert.octylthio)-propan-2-ol, 1-[2,2,4-trimethyl-1,2,3,4-tetrahydroquinol-1-yl]-3-(p-tolyloxy)-propan-2-ol, 1-[2,2,4-trimethyl-1,2,3,4-tetrahydroquinol-1-yl]-3-(o-tolyloxy)-propan-2-ol, 1-(4-butylphenyl)-2,4-diethyl-6,7-dimethoxy-2-methyl-1,2,3,4-tetrahydroquinoline, 1-(oleyl)-2,4-diphenyl-4-methyl-1,2,3,4-tetrahydroquinoline, 1-(3-methoxy-pentadec-2-yl)-4-benzyl-6,7-dichloro-2,4-dimethyl-1,2,3,4-tetrahydroquinoline, 1,1-bis-[1-(3′,5′-dimethyl-phenyl)-2,2,4-trimethyl-1,2,3,4-tetrahydroquinol-6-yl]-methane, 1,1-bis-[1-(2′-hydroxyethyl)-2,4-diethyl-2-methyl-1,2,3,4-tetrahydroquinol-6-yl]-methane, 1,1-bis-[1,2-diethyl-2,4-dimethyl-1,2,3,4-tetrahydroquinol-6-yl]-cyclohexane.

The preparation of the compounds of the formulae I and II is effected in a conventional manner.

For instance, aniline and a methyl ketone can be reacted in a molar ratio of 1:2 as described in Org. Synthesis, Coll. Vol. III, p. 329–32, or in U.S.-A-2,846,435. The resulting N-unsubstituted 1,2,3,4-tetrahydroquinoline can be reacted in a conventional manner with customary alkylating, arylating or benzylating agents, e.g. dimethyl sulfate, allyl bromide, iodobenzene or benzyl chloride, to the compounds of the formula I.

The compounds of the formula II can be prepared as described in U.S.-A-3,247,211.

Novel compounds of the formula I or II can be prepared in a similar manner.

The compounds according to the invention of the formulae I, II and IV are very highly suitable for use as antioxidants in lubricants, hydraulic oils and metal-working fluids, in particular in lubricants and hydraulic oils, especially in lubricants.

The present invention therefore also provides a method of using the compounds of the formula I, II and IV as antioxidants in lubricants, hydraulic oils or metal-working fluids.

The compounds of the formulae I and II are sufficiently soluble in lubricants, hydraulic oils and metal-working fluids and are preferably added to these substrates in an amount of 0.1–2.5% by weight, based on the total weight of the lubricant, hydraulic oil or metal-working fluid composition.

These lubricant, hydraulic oil or metal-working fluid systems can be polar or apolar. The selection criteria are based on the solubility properties of the corresponding compounds. The lubricants, hydraulic fluids and metal-working fluids which come into consideration are known to those skilled in the art and are described for example in "Schmiermittel Taschenbuch" (Hüthig Verlag, Heidelberg, 1974), in "Ullmanns Encyclopädie der technischen Chemie", volume 13, pages 85–94 (Verlag Chemie, Weinheim, 1977) and D. Klamann "Schmierstoffe und verwandte Produkte" pages 158–174 (Verlag Chemie, Weinheim, 1982) respectively.

Particularly suitable are in addition to mineral oils for example poly-α-olefins, ester lubricants, phosphate, glycols, polyglycols and polyalkylene glycols and mixtures thereof with water.

The lubricants, hydraulic fluids and metal-working fluids can additionally contain other additives which are added to further improve the basic properties of these substances; they include: further antioxidants, metal passivators, rust inhibitors, viscosity index improvers, setting point reducers, dispersants, detergents and also high pressure additives and antiwear additives.

Examples of phenolic antioxidants

1. Alkylated monophenols 2,6-Di-tert-butyl-4-methylphenol, 2,6-di-tert-butylphenol, 2-tert-butyl-4,6-dimethylphenol, 2,6-di-tert-butyl-4-ethylphenol, 2,6-di-tert-butyl-4-ethylphenol, 2,6-di-tert-butyl-4-n-butylphenol, 2,6-di-tert-butyl-4-isobutylphenol, 2,6-di-cyclopentyl-4-methylphenol, 2-(α-methylcyclohexyl)-4,6-di-methylphenol, 2,6-di-octadecyl-4-methylphenol, 2,4,6-tricyclohexylphenol, 2,6-di-tert-butyl-4-methoxymethylphenol, o-tert-butylphenol.

2. Alkylated hydroquinones 2,6-Di-tert-butyl-4-methoxyphenol, 2,5-di-tert-butyl-hydroquinone, 2,5-di-tert-amyl-hydroquinone, 2,6-diphenyl-4-octadecyloxyphenol

3. Hydroxylated thiodiphenyl ethers 2,2'-Thio-bis-(6-tert-butyl-4-methylphenol), 2,2'-thio-bis-(4-octylphenol), 4,4'-thio-bis-(6-tert-butyl-3-methylphenol), 4,4'-thio-bis-(6-tert-butyl-2-methylphenol).

4. Alkylidenebisphenols 2,2'-Methylene-bis-(6-tert-buty-4-methylphenol), 2,2'-methylene-bis-(6-tert-butyl-4-ethylphenol), 2,2'-methylene-bis-[4-methyl-6-(α-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4-iso-butylphenol), 2,2'-methylene-bis-[6-(α-methylbenzyl)-4-nonylphenol], 2,2'-methylene-bis-[6-(α,α-dimethylbenzyl)-4-nonylphenol]], 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenyl)-butane, 2,6-di-(3-tert-butyl-5-methyl-2-hydroxybenzyl)-4-methylphenol, 1,1,3-tris-(5-tert-butyl-4-hydroxy-2-methyl-phenyl)-3-n-dodecyl-mercaptobutane, ethylene glycol bis-[3,3-bis-(3'-tert-butyl-4'-hydroxyphenyl) butyrate], di-(3-tert-butyl-4-hydroxy-5-methylphenyl)-dicyclopentadiene, di-[2-(3'-tert-butyl-2'-hydroxy-5'-methyl-benzyl)-6-tert-butyl-4-methylphenyl] terephthalate.

5. Benzyl compounds 1,3,5-Tri-(3,5-di-tert-butyl-4-hydroxybenzyl)-2,4,6-trimethylbenzene, di-(3,5-di-tert-butyl-4-hydroxybenzyl) sulfide, iso-octyl 3,5-di-tert-butyl-4-hydroxybenzyl-mercaptoacetate, bis-(4-tert-butyl-3-hydroxy-2,6-dimethylbenzyl)-dithiol terephthalate, 1,3,5-tris-(3,5-di-tert-butyl-4-hydroxybenzyl) isocyanurate, 1,3,5-tris-(4-tert-butyl-3-hydroxy-2,6-dimethylbenzyl) isocyanurate, di-octadecyl 3,5-di-tert-butyl-4-hydroxybenzyl-phosphonate, calcium salt of monoethyl 3,5-di-tert-butyl-4-hydroxybenzyl-phosphonate.

6. Acylaminophenols

4-Hydroxylauranilide, 4-hydroxystearanilide, 2,4-bis-octyl-mercapto-6-(3,5-di-tert-butyl-4-hydroxyanilino)-s-triazine, octyl N-(3,5-di-tert-butyl-4-hydroxyphenyl)-carbamate.

7. Esters of β-(3,5-di-tert-butyl-4-hydroxyphenyl)-propionic acid with monohydric or polyhydric alcohols, for example with

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | dihydroxyethyloxamide |

8. Esters of β-(5-tert-butyl-4-hydroxy-3-methylphenyl)-propionic acid with monohydric or polyhydric alcohols, for example with

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | dihydroxyethyloxamide |

9. Amides of β-(3,5-di-tert-butyl-4-hydroxyphenyl)-propionic acid for example N,N'-di-(3,5-di-tert-butyl-4-hydroxyphenylpropionyl)-hexamethylenediamine, N,N'-di-(3,5-di-tert-butyl-4-hydroxyphenylpropionyl)-trimethylenediamine, N,N-di-(3,5-di-tert-butyl-4-hydroxyphenylpropionyl)-hydrazine.

Examples of amine antioxidants

N,N'-Di-isopropyl-p-phenylenediamine, N,N'-di-sec-butyl-p-phenylenediamine, N,N'-bis(1,4-dimethyl-pentyl)-p-phenylenediamine, N,N'-bis(1-ethyl-3-methylpentyl)-p-phenylenediamine, N,N'-bis(1-methyl-heptyl)-p-phenylenediamine, N,N'-diphenyl-p-phenylenediamine, N,N'-di-(naphthyl-2)-p-phenylenediamine, N-isopropyl-N'-phenyl-p-phenylenediamine, N-(1,3-dimethylbutyl)-N'-phenyl-p-phenylenediamine, N-(1-methyl-heptyl)-N'-phenyl-p-phenylenediamine, N-cyclohexyl-N'-phenyl-p-phenylenediamine, 4-(p-toluene-sulfonamido)-diphenylamine, N,N'-di-methyl-N,N'-di-sec-butyl-p-phenylenediamine, diphenylamine, 4-isopropoxy-diphenylamine, N-phenyl-1-naphthylamine, N-phenyl-2-naphthylamine, octylated diphenylamine, 4-n-butyl-aminophenol, 4-butyrylamino-phenol, 4-nonanoylamino-phenol, 4-dodecanoylamino-phenol, 4-octadecanoylamino-phenol, di-(4-methoxy-phenyl)-amine, 2,6-di-tert-butyl-4-dimethylaminomethyl-phenol, 2,4'-diamino-diphenylmethane, 4,4'-diamino-diphenylmethane, N,N,N',N'-tetramethyl-4,4'-diamino-diphenylmethane, 1,2-di[(2-methyl-phenyl)-amino]-ethane, 1,2-di-(phenylamino)-propane, (o-tolyl)-biguanide, di-[4-(1',3'-di-methyl-butyl)-phenyl)amine, tert-octylated N-phenyl-1-naphthylamine, mixture of monoalkylated and dialkylated tert-butyl-/tert-octyldiphenylamines.

Examples of metal passivators are for copper, for example: triazole, benzotriazole and derivatives thereof, 2-mercaptobenzothiazole, 2,5-dimercaptothiadiazole, salicylidenepropylenediamine, salts of salicylaminoguanidine.

Examples of rust inhibitors are (a) organic acids, their esters, metal salts and anhydrides, for example: N-oleoyl-sarcosine, sorbitan monooleate, lead naphthenate, dodecenylsuccinic anhydride, monoalkenyl succinates, 4-nonylphenoxyacetic acid.
(b) nitrogen-containing compounds, for example:
  I. primary, secondary or tertiary aliphatic or cycloaliphatic amines and amine salts of organic and inorganic acids, for example oil-soluble alkylammonium carboxylates.
  II. heterocyclic compounds, for example: substituted imidazolines and oxazolines.
(c) Phosphorus-containing compounds, for example: amine salts of partial phosphoric esters.
(d) Sulfur-containing compounds, for example: barium di-nonylnaphthalenesulfonate, calcium petroleumsulfonates.

Examples of viscosity index improvers are for example polymethacrylates, vinylpyrrolidone/methacrylate copolymers, polybutenes, olefin copolymers, styrene/acrylate copolymers.

Examples of setting point reducers are for exmple polymethacrylate, alkylated naphthalene derivatives.

Examples of dispersants/surfactants are, for example

Polybutenylsuccinimides, polybutenylphosphonic acid derivatives, basic magnesium, calcium and barium sulfonates and phenolates.

Examples of antiwear additives are for example

Sulfur- and/or phosphorus- and/or halogen-containing compounds, such as sulfurized vegetable oils, zinc dialkyl dithiophosphates, tritolyl phosphate, chlorinated paraffins, alkyl and aryl disulfides.

Example 1

350 g of 2,2,4-trimethyl-1,2,3,4-tetrahydroquinoline, 2000 ml of ethanol and 110 g of ethylene oxide are heated at 180° C. in an autoclave for 12 hours. The ethanol is then distilled off, and the crystals of 1-(2-hydroxyethyl)-2,2,4-trimethyl-1,2,3,4-tetrahydroquinoline are filtered off. Recrystallization from ethanol gives a product having a melting point of 73°–75° C.

The method of Example 1 is repeated to prepare Examples 2–6.

Example 7

52.6 g of 2,2,4-trimethyl-1,2,3,4-tetrahydroquinoline and 37.2 g of dimethyl methanephosphonate are heated together for 5 hours at 160° C. in a slow stream of nitrogen. Thereafter the reaction mixture is cooled down to 60° C. and taken up in 100 ml of toluene, and the mixture is brought to an alkaline pH with 130 g of 10% NaOH solution. The organic phase is separated off, washed twice with 100 ml of water each time and evaporated at 80° C. in a rotary evaporator. The residue is then dried at 60° C. in a high vacuum. 54.1 g are obtained of a clear, light brown oil having a boiling point of 274° C. at 1013 mbar.

Examples 8 to 11 are obtained in a similar manner.

Example 12

35.1 g of 12,2,4-trimethyl-1,2,3,4-tetrahydroquinoline are introduced into a flask and heated to 90° C., and 47.6 g of tert.-nonyl glycidyl thioether are added dropwise with stirring. After everything has been added, the mixture is stirred at 90° C. for a further 0.5 hour. An oil having a boiling point of 185° C. at 0.03 mbar is obtained.

Example 13 is prepared in a similar manner.

TABLE 1

| Example number | Compound | Melting/boiling point |
|---|---|---|
| 1 | 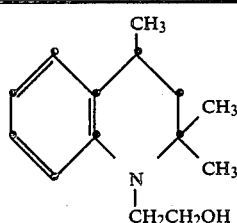 | 73–75° C. |
| 2 | 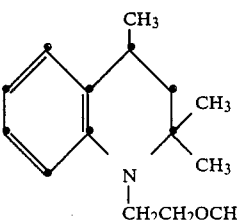 | 110–112° C./0.4 mbar |

TABLE 1-continued
| Example number | Compound | Melting/boiling point |
|---|---|---|
| 3 | 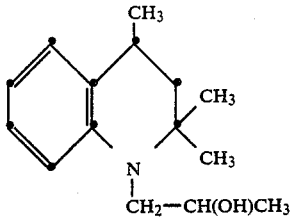 | 130–134° C./ 0.53 mbar |
| 4 | 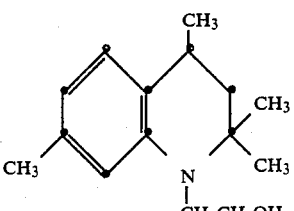 | 78–79° C. |
| 5 | 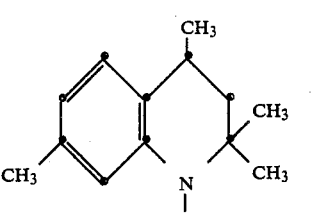 | 120° C./ 0.2 mbar |
| 6 | 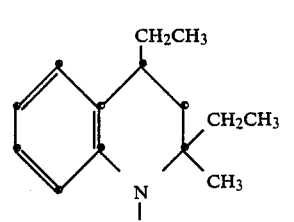 | 130–135° C./ 0.13 mbar |
| 7 | 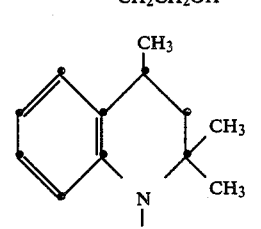 | 274° C./ 1013 mbar |
| 8 | 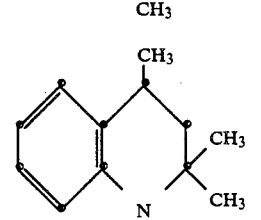 | 84–86° C./ 0.2 mbar |
| 9 | 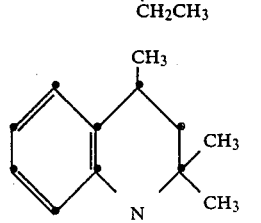 | 283° C./ 1013 mbar |

TABLE 1-continued

| Example number | Compound | Melting/ boiling point |
|---|---|---|
| 10 | [structure: dihydroquinoline with CH2CH3 at 4-position, two CH2CH3 and CH3 at 2-position, N-CH3] | 105° C./ 0.27 mbar |
| 11 | [structure: dihydroquinoline with CH2CH3 at 4-position, CH2CH3 and CH3 at 2-position, N-CH2-phenyl] | 296° C./ 1013 mbar |
| 12 | [structure: dihydroquinoline with CH3 at 4-position, two CH3 at 2-position, N-CH2CH(OH)CH2S-(tert.-C9H19)] | 185° C./ 0.03 mbar |
| 13 | [structure: dihydroquinoline with extra CH3 on ring, CH3 at 4-position, two CH3 at 2-position, N-CH2CH(OH)CH2S-(tert.-C9H19)] | 194° C./ 0.03 mbar |

Example 14

Thin-Film Oxygen Uptake Test (TFOUT)

This test is a modified version of the "rotary bomb oxidation test for mineral oils" (ASTM D 2272). It is described in detail in "C. S. Ku and S. M. Hsu, A Thin-Film Oxygen Uptake Test for the Evaluation of Automotive Crankcase Lubricants, Lubrication Engineering, vol. 40 (2), 75–83 (1984)". The test oil used is a motor oil which is based on mineral oil and contains half the customary amount of zinc dithiophosphate (0.75%; zinc content 0.06%, based on the motor oil).

The compound prepared is tested in the motor oil described in the presence of 2% of water, in the presence of a liquid oxidized nitrated fraction of a motor petrol as catalyst (4% starting concentration) and in the presence of a liquid metal naphthenate as further catalyst (4% starting concentration). The water and the two liquid catalyst substances are supplied by the National Bureau of Standards (NBS) as No. Standard Reference Material 1817 together with a certificate of analysis. The test terminates with an appreciable break in the pressure/time diagram. The results indicated in Table 2 signify the time (in minutes) to the break in the pressure-time diagram.

Long times correspond to high stabilizer activity. Concentration of stabilizer: 0.5% by weight, based on the oil.

TABLE 2

| Stabilizer | Minutes to appreciable pressure loss |
|---|---|
| none | 76 |
| Example 1 | 199 |
| Example 3 | 185 |
| Example 4 | 197 |
| Example 6 | 186 |
| Example 7 | 220 |
| Example 8 | 218 |
| Example 9 | 200 |

What is claimed is:
1. A composition which comprises
   (a) at least one lubricant, hydraulic oil or metal-working fluid based on mineral oil or synthetic oil, and
   (b) 0.05–5% by weight, based on the total weight of the lubricant, hydraulic oil or metal-working fluid composition, of at least one compound of formula V

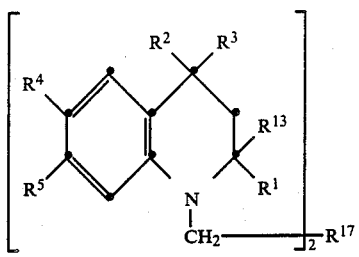
(V)

in which $R^1$ and $R^2$ are independently of each other $C_1$–$C_8$-alkyl, unsubstituted or $C_1$–$C_{12}$-alkyl-, Cl-, Br-, I-, $NO_2$-, OH- or $C_1$–$C_{12}$-alkoxy-substituted phenyl or naphthyl, or benzyl, $R^3$ is hydrogen or methyl, $R^4$ and $R^5$ are independently of each other hydrogen, methyl, methoxy, -Cl or -$NO_2$, $R^{13}$ is hydrogen or methyl, and $R^{17}$ is —$C_xH_{2x}$—, where x is 0 to 10, or $R^{17}$ is —CH=CH—.

2. A composition according to claim 1, wherein component (a) is a lubricant or a hydraulic oil.

3. A process for stabilizing a lubricant, hydraulic oil or metal-working fluid against oxidative degradation which comprises incorporating into said lubricant, hydraulic oil or metal-working fluid 0.05–5% by weight, based on the total weight of lubricant, hydraulic oil or metal-working fluid composition, of at least one compound of formula V according to claim 1.

* * * * *